ROSE PLANT
Filed Oct. 2, 1968 2 Sheets-Sheet 1
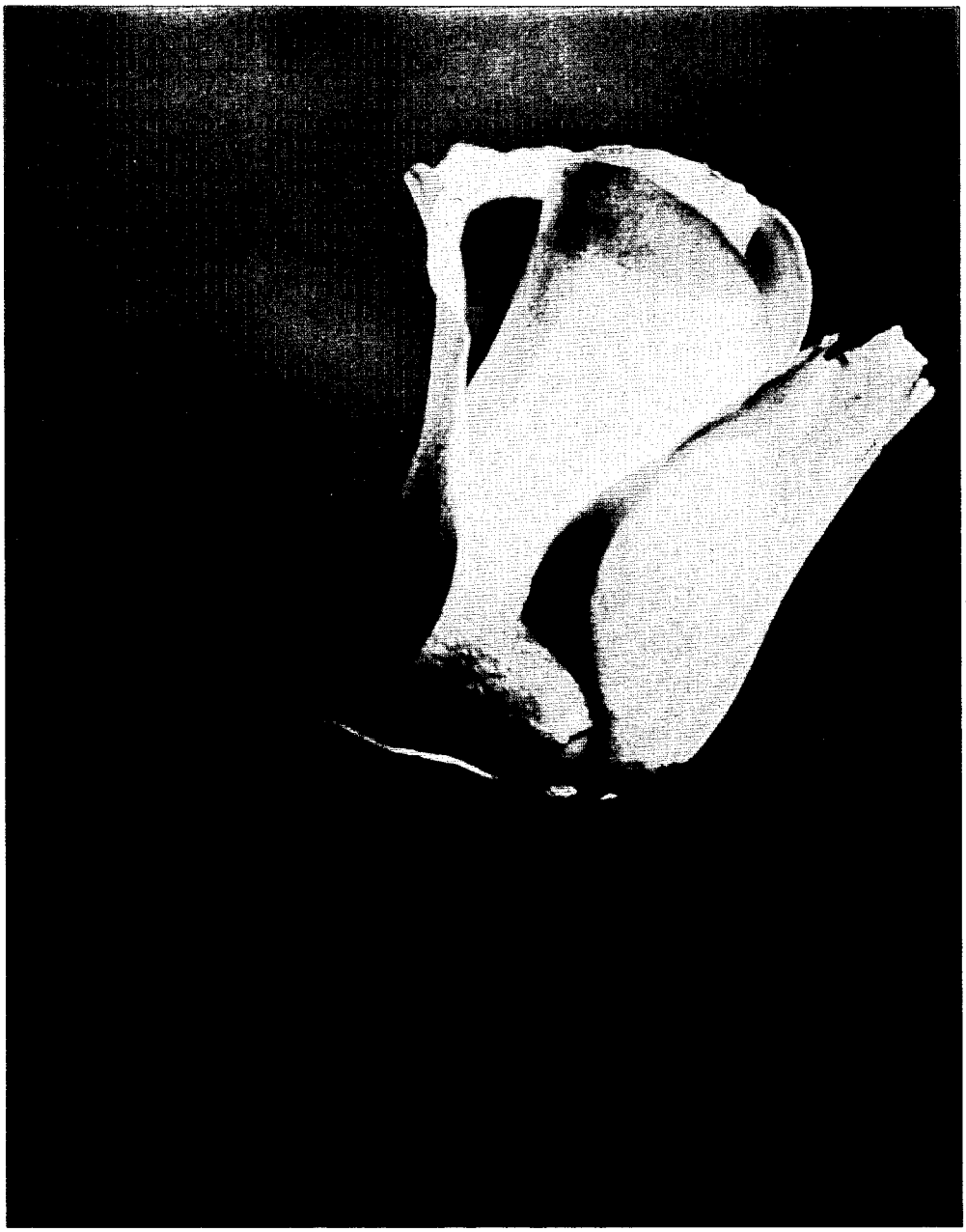
Inventor.
Michel Kriloff
By: Robbins Robb
Attorneys.

ROSE PLANT
Filed Oct. 2, 1968 2 Sheets-Sheet 2
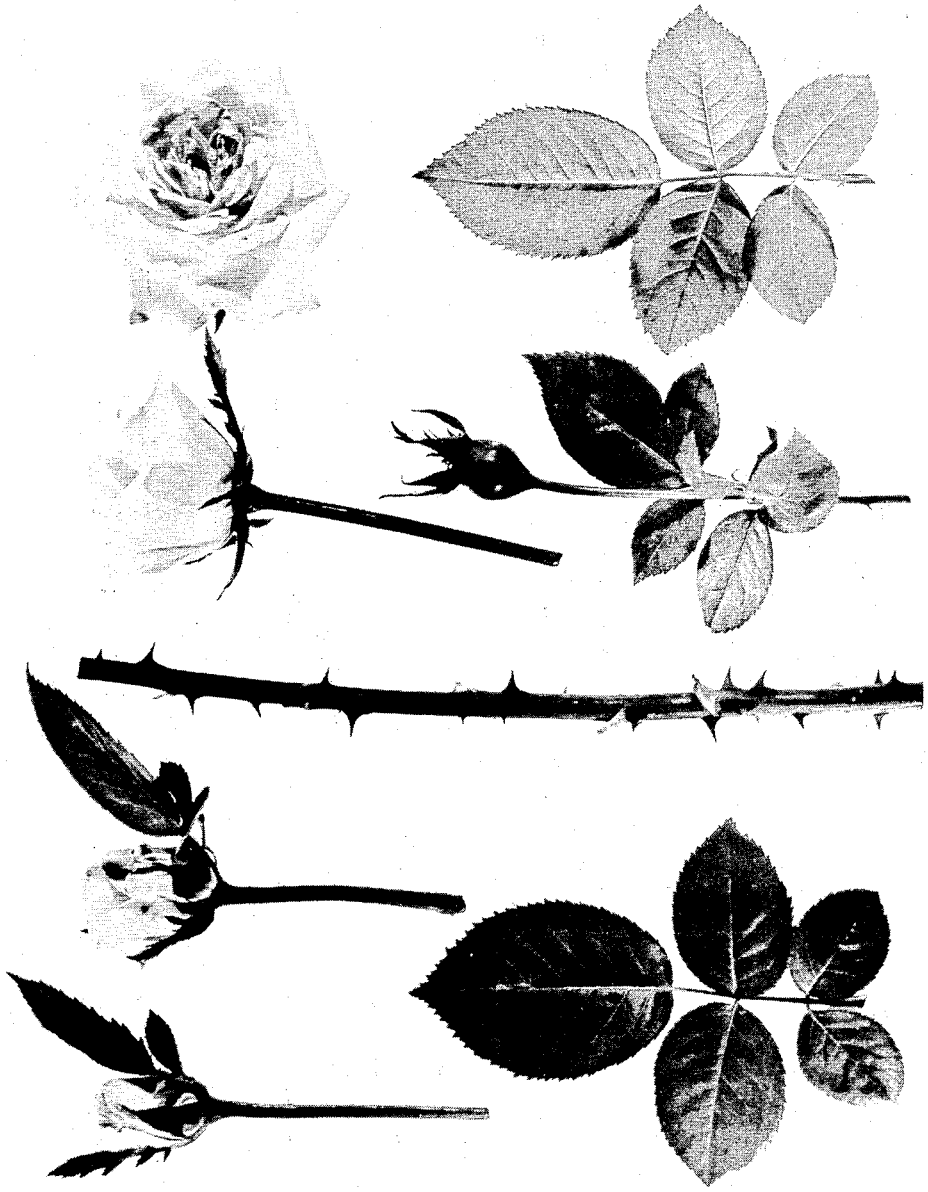
Inventor.
Michel Kriloff
By: Robb & Robb
Attorneys.

United States Patent Office

Plant Pat. 3,011
Patented Jan. 5, 1971

3,011
ROSE PLANT

Michel Kriloff, Chemin de Saint Maymes, Antibes, Alpes-Maritimes, France

Filed Oct. 2, 1968, Ser. No. 764,973
Claims priority, application France, Oct. 12, 1967, 124,266
Int. Cl. A01h *5/00*
U.S. Cl. Plt.—18 1 Claim

The present invention relates to a new and distinct variety of rose plant of the hybrid tea class, which was originated by me by crossing the rose variety known in France as "Super Star" (better known in the United States as "Tropicana"—U.S. Plant Pat. No. 1,969) with the rose variety known as "Romantica" (unpatented).

As the result of this breeding, I have produced a new and improved rose variety which is distinguished from its parents, as well as from all other varieties of which I am aware, as evidenced by the following unique combination of characteristics which are outstanding in the new variety:

(1) A regular and good plant habit;

(2) A healthy leaf system, with the foliage being borne in abundance;

(3) An abundant and continuous flowering habit, particularly during the winter months;

(4) Blooms of elegant form and of average size and usually born singly and erect on sturdy, relatively stiff stems, with the blooms having good petalage;

(5) A distinctive, attractive, delicate and warm, pale pearly pink general color tonality of the flowers;

(6) Good resistance to frost and other bad weather conditions and to diseases commonly attributed to roses, as compared with other rose varieties grown in France under the same conditions;

(7) Excellent adaptability to various grafting stocks under widely varying climate and soil conditions;

(8) Excellent adaptability to forced cultivation under glass;

(9) Good shipping qualities; and

(10) Excellent lasting qualities of the flowers as cut flowers.

Asexual reproduction of my new variety, particularly by so-called shield-bud grafting, as performed by me at Antibes, France, shows that the foregoing characteristics and distinctions come true to form and are established and transmitted through succeeding propagations.

The accompanying drawings show a typical flower specimen of my new variety in the opening bud stage of development, as depicted in color as nearly true as it is reasonably possible to make the same in a color illustration of this character, and also the drawings show in black and white typical vegetative and flower specimens in different stages of development.

The following is a detailed description of my new rose variety, with color terminology in accordance with Rene Oberthur's Repertoire de Couleurs, except where general color terms of ordinary dictionary significance are obvious:

Type: Hardy; bush; seedling; for outdoor and for greenhouse cultivation and particularly for cut flower use.
Class: Hybrid tea.
Breeding: Seedling.
*Seed parent.*—"Super Star" (known in the United States as "Tropicana").
*Pollen parent.*—"Romantica."
Locality where grown and observed: In the spring in a hothouse, at Antibes, France.

PLANT

Height: From 150 cm. to 180 cm. from the ground to the tip of the stems for one-year grafts on indica major.
Habit: Bushy; erect; dense and abundant foliage.
Branches:
*Young shoots.*—Color: Reddish.
*Mature.*—Color: From Meadow Green, Hue 4, Plate 268 to Spinach Green, Hues 2–3, Plate 270.
*Length.*—From 50 cm. to 110 cm., but sometimes shorter or longer, depending on the season and the method of pruning, with average length from about 75 cm. to 80 cm.
*Bark.*—Thin; smooth between thorns.
*Thorns.*—More numerous on the lower portion of the branches, with largest unequally distributed from the base of the branch to the first leaf below the bloom, and the smallest disappearing toward the upper portion of the branch; large and small thorns intermixed. Shape: Triangular, with a sharp point inclined slightly downward. Quantity: Average. Size: Variable; length—average from about 6 mm. to 10 mm.; width—average from about 6 mm. to 8 mm.; thickness—average from about 2 mm. to 3 mm. Color: Reddish on young shoots, progressing to from Brownish Green, Plate 296 to Nut Brown at extreme maturity.
*Flower-bearing stems.* — Moderately numerous; straight; sturdy.
Foliage:
*Leaves.*—Numerous; cover the plant and the flower-bearing stems with elegance. Form: Usually compound of 7–5, rarely 3, leaflets from base of branch to tip, with 5 leaflets on the rachis at regular intervals arranged in opposing pairs and with 1 terminal leaflet. Size: From average to large length—from 120 mm. to 140 mm., and sometimes from 170 mm. to 180 mm., from the branch point to the point of the terminal leaflet; width—from 80 mm. to 90 mm., and sometimes from 120 mm. to 130 mm., between tips of opposite leaflets below the terminal leaflet.
*Leaflets.*—Shape: Ovoid; symmetrical to central vein; rather deeply serrated about margins. Size: Terminal leaflet is the largest and basal leaflets are always small, with successive pairs diminishing progressively from about 50 mm. to 30 mm. to about 40 mm. to 25 mm. on the average, with largest ranging between 65 mm. to 45 mm. and 50 mm. to 35 mm., with basal leaflets ranging between 25 mm. to 15 mm. and 30 mm. to 20 mm.
*Color (mature).*—Upper surface: American Green, Hues 3–4, Plate 237. Reverse surface: Pea Green, Hue 1, Plate 277.
*Color (on young shoots).*—Reddish.
*Surface.*—Upper: Glabrous; smooth; with thin furrowed veins. Under: Opaque; veins protrude somewhat.
*Rachis.*—Sturdy; almost cylindrical; with a visible groove on the obverse side; divided into regular sections between the insertions of the petioles of the leaflets.
*Stipules.*—Adnate to the base of the rachis over a length varying from 15 mm. to 25 mm., and then divided into 2 auricles.

FLOWER

Peduncle: Course; stiff; substantially uniform in section; well detached; upper half generally smooth; lower half studded irregularly with small thorns of unequal size;

average length about 100 mm. from the flower to the first leaf.

Bud:

*Shape.*—Elongated ovoid, with a sharp tip.

*External guard petals.*—Color: Near Saffron Rose, Hue 2, Plate 124.

*Size (on an everage stem and when sepals start to loosen).*—Length: From 22 mm. to 28 mm. Width: From about 17 mm. to 28 mm.

*Sepals.*—Detached from corolla rather early and gradually assume a horizontal position as the flower opens.

Flower: Average size and duplicature; opening forms at all stages correspond to the classic type of rose flower; petals roll outward as opening progresses and impart to the flower a rounded rosaceous form as long as flower lasts.

*Size.*—About 100 mm. in diameter.

*Habit.*—Erect; borne singly; with straight axis along the stem.

*Fragrance.*—Fruity.

*Color.*—General color tonality over all is Rose Salmon Carmine, Plate 124 with warm and luminous brilliance over the heart of the flower.

*Calyx.*—Conical at the base of the calyx or receptacle, suggesting an inverted funnel with the narrower opening being the upper portion of the peduncle.

*Receptacle.*—Small. Color: Pale Green.

*Sepals.*—5 in number, with 3 having numerous foliaceous appendages which are more or less glandular and the other 2 having solid edges; intercalated, with their positions as follows: 2 leaflike sepals side-by-side, 1 sepal with solid edges, 1 leaflike sepal, and one sepal with solid edges; of the 3 leaflike sepals, one is often longer and more fringed than the others, with the terminal portion being elongated and with serrated edges more pronounced in the lower portion; sepals with solid edges have elongated triangle shape, curve inward and terminate in a very sharp point. Color: Reverse surface—Near Meadow Green, Hue 5, Plate 268; obverse surface—Downy whitish, except for the terminal portion of the leaflike sepals which are the same color as the bush leaf, i.e. American Green, Hue 4, Plate 237. Base width: About 10 mm. Total length: Solid edged sepals—from about 25 mm. to 30 mm.; leaflike sepals—from about 30 mm. to 40 mm.

*Corolla.*—Petals: Average number; very firm consistency, with venules visible on both surfaces; obverse surface is smooth and satiny; reverse surface is more silky than satiny, presenting a median line of creamy white dividing the petal into two equal parts lengthwise; petals regularly disposed inside corolla, with limbus very slack to the center of the flower; petals become smaller toward the center of the flower, and at the center, there are a few asymmetrical, irregular flowers; limbus is elliptical, but sometimes almost round, with upper portion turned outward; wide claw (about ⅓ of the height of the petal), having its color near Sulphur White, Hue 2, Plate 14 which is more pronounced in the extreme lower part and more attenuated but of the same hue toward the upper part of the limbus; the width of the claw, together with the blending of pale yellow and salmon pink colors, accounts for the exceptional luminous quality of the flower. Size: Outer petals—length: from 50 mm. to 55 mm.; width: from 40 mm. to 45 mm.; claw: 13 mm.; Inner petals—length: from 40 mm. to 45 mm.; width: about 40 mm.; claw: from 15 mm. to 18 mm. Number of petals: From about 30 to 35, with about 10 petaloids at the center of the flower. Color: Saffron Pink, Hue 1, Plate 124 over upper part, blending to Salmon Carmine, Plate 124.

REPRODUCTIVE ORGANS

Stamens: Unequal length; arranged very irregularly in a crown about the pistils; from about 100 to 120 in number.

Filaments:

*Color.*—Reddish, except in the first row where there are a few of uniformly yellow color.

Anthers: Average size; fertile.

*Color.*—Darker yellow on the edges and lighter at the center.

Pistils: From about 90 to 100 in number.

Styles: Rather numerous; thin; unequal length.

*Color.*—Reddish upper parts.

Receptacles:

*Size.*—From small to average.

*Form.*—Conical.

*Color.*—Delicate green.

Fruit: Good production.

Hips: Average size; rounded; at this stage, the sepals form a horizontal star, and the achenes are totally or partly visible and extend beyond the calyx tube.

GENERAL OBSERVATIONS

Inflorescence: Uniflorous and favorable for cut flower production.

Disease resistance: Very good resistance to the usual rose diseases, as determined by comparison with other varieties grown under the same conditions at Antibes, France.

Weather resistance: Very good resistance to frost and bad weather.

Lasting qualities: Excellent lasting qualities as cut flowers.

Shipping qualities: Very good.

I claim:

1. A new and distinct variety of rose plant of the hybrid tea class, substantially as herein shown and described, characterized particularly as to novelty by the unique combination of a regular and good plant habit, a healthy leaf system, with the foilage being borne in abundance, an abundant and continuous flowering habit, particularly during the winter months, blooms of elegant form and of average size and usually borne singly and erect on sturdy, relatively stiff stems, with the blooms having good petalage, a distinctive, attractive, delicate and warm, pale pearly pink general color tonality of the flowers, good resistance to frost and other bad weather conditions and to diseases commonly attributed to roses, as compared with other rose varieties grown in France under the same conditions, excellent adaptability to various grafting stocks under widely varying climate and soil conditions, excellent adaptability to forced cultivation under glass, good shipping qualities, and excellent lasting qualities of the flowers as cut flowers.

No references cited.

ROBERT E. BAGWILL, Primary Examiner